United States Patent [19]

Gauhl et al.

[11] 4,237,221

[45] Dec. 2, 1980

[54] PROCESS FOR OBTAINING MALTOSE PHOSPHORYLASE AND β-PHOSPHOGLUCOMUTASE AND METHOD OF DETERMINING α-AMYLASE USING SAME

[75] Inventors: Helmgard Gauhl; Hans Seidel, both of Tutzing, Fed. Rep. of Germany

[73] Assignee: Boehringer Mannheim GmbH, Mannheim, Fed. Rep. of Germany

[21] Appl. No.: 953,723

[22] Filed: Oct. 20, 1978

[30] Foreign Application Priority Data

Oct. 26, 1977 [DE] Fed. Rep. of Germany ....... 2748036

[51] Int. Cl.³ .......................... C12N 9/12; C12Q 1/32; C12Q 1/40; C12Q 1/48
[52] U.S. Cl. ...................................... 435/15; 435/22; 435/26; 435/194
[58] Field of Search ..................... 435/15, 22, 26, 194; 195/66, 99, 103.5 R, 103.5 S

[56] References Cited

U.S. PATENT DOCUMENTS

| | | | |
|---|---|---|---|
| 4,036,697 | 7/1977 | Pierre et al. | 435/15 |
| 4,162,194 | 7/1979 | Pierre et al. | 435/15 |

OTHER PUBLICATIONS

Kamogawa et al., *Agr. Biol. Chem.*, 37(12), (1973), 2813–2819.
Wood et al., *Biochem. J.*, 78, (1961), 204–209.
Kamogawa et al., *Anal. Biochem.*, 57, (1974), 303–305.

*Primary Examiner*—Esther M. Kepplinger
*Attorney, Agent, or Firm*—Sprung, Felfe, Horn, Lynch & Kramer

[57] ABSTRACT

The present invention provides a process for obtaining maltose phosphorylase and/or β-phosphoglucomutase from micro-organisms, wherein the starting material used is selected from *Lactobacillus brevis* DSM 20054, NCIB 8836, 8561 and 8562, *Lactobacillus plantarum* DSM 20174 and 43, *Lactobacillus reuteri* DSM 20016, *Lactobacillus fermentum* DSM 20052, *Streptococcus spec.* DSM 1118, DSM 119, DSM 1120 and DSM 1121.

The present invention also provides a composition and process for determining α-amylase, wherein maltose phosphorylase and β-phosphoglucomutase obtained by such a process is used, as a crude extract or in an enriched form, optionally with the addition of α-glucose-1,6-diphosphate and of divalent manganese ions.

10 Claims, No Drawings

PROCESS FOR OBTAINING MALTOSE PHOSPHORYLASE AND β-PHOSPHOGLUCOMUTASE AND METHOD OF DETERMINING α-AMYLASE USING SAME

The present invention relates to a process for obtaining maltose phosphorylase and/or β-phosphoglucosemutase from micro-organisms, and to the use of the enzymes so obtained.

It is known that maltose phosphorylase occurs in *Neisseria meningitidis* (J. Biol. Chem., 199, 153/1952), in non-identified beer *Lactobacilli* (Biochem. J., 78, 204/1961) and in *Lactobacillus brevis* IFO 3345=ATCC 8287 (Agr. Biol. Chem., 37, 2813/1973) and can be obtained therefrom.

β-Phosphoglucose mutase is known to occur in rabbit muscles, yeast and *Neisseria meningitidis* (J. Biol. Chem., 236, 2186/1961), as well as in *Lactobacillus brevis* ATCC 8287.

The two above-mentioned enzymes are of commercial interest since they can together be employed for the determination of α-amylase, which is a diagnostically very important enzyme. This determination is based upon the hydrolysis of starch by the α-amylase, with the formation of maltose. The maltose thus formed is split by maltose phosphorylase (MP), in the presence of phosphate, into glucose and β-glucose-1-phosphate, the latter is converted by β-phosphoglucose mutase (βPGM) into α-glucose-6-phosphate which then, in known manner, in the presence of glucose-6-phosphate dehydrogenase (G6PDH), reduces nicotinamide-adenine dinucleotide (NAD) to its reduced form (NADH) and is thereby itself converted into 6-phosphogluconate. The NADH formed is thus a measure for the α-amylase activity.

For clinical tests with combined enzymatic reactions in which, therefore, several enzymes are employed, it is of decisive importance whether the required enzymes are easily obtainable and can readily be brought into a form suitable for the analysis. Thus, the cost of such enzymatic determinations is substantially determined by the cost of the enzymes employed. It is especially favorable when, from a single starting material, several enzymes to be employed for a particular test can be obtained simultaneously.

Amongst previously known starting materials, the two above-mentioned enzymes occur together in *Neisseria meningitidis* which permits there use in an α-amylase test without previous separation. However, it is a considerable disadvantage that this micro-organism is extremely dangerous and virulent and can only be employed with the greatest of precautionary measures as a source of enzymes to be used industrially. Furthermore, the activities of the enzymes found in this micro-organism are unsatisfactory. *Lactobacillus brevis* ATCC 8287 additionally contains α-glucosidase, an enzyme which adversely affects the use of the other two enzymes, which means that a purification is unavoidable.

The present invention provides a process for obtaining MP and optionally also of β-PGM which avoids the use of the dangerous *Neisseria meningitidis* and permits a simple production of these enzymes from an easily obtainable, harmless starting material. The invention further provides a process of the above-mentioned type using a micro-organism, the crude extract of which can be employed directly for the determination of α-amylase since it contains sufficiently high activities of the enzymes MP and β-PGM and thus does not require any purification.

The process of the present invention for obtaining maltose phosphorylase and/or β-phosphoglucomutase from micro-organisms, comprises using as the starting material a micro-organism selected from *Lactobacillus brevis* NCIB 8836, 8561, 8562, ATCC 8287 and DSM 20054, *Lactobacillus plantarum* DSM 20174 and 43, *Lactobacillus reuteri* DSM 20016, *Lactobacillus fermentum* DSM 20052, *Streptococcus spec.* DSM 1118, 1119, 1120 and DSM 1121.

Surprisingly, we have found that the above-mentioned micro-organisms contain the two mentioned enzymes in high activity and that the two enzymes can easily be obtained therefrom. It is thereby also possible to obtain the two individual enzymes in separated form by isolating them, according to the usual methods of enzyme enrichment, from the extracts of these micro-organisms, followed by purification, for example by removing impurities by polyethyleneimine precipitation, fractionally precipitating with salts, such as ammonium sulphate, treating with adsorbents and exchange chromatography, especially with the use of weakly basic exchangers based upon cross-linked dextran or upon cellulose.

However, for use for the determination of α-amylase, the crude extracts of the above-mentioned micro-organisms can be used directly. For this purpose, the micro-organisms can be digested by conventional physical methods, for example with ultrasonics, by high pressure dispersion, by grinding or the like, insoluble fragments are removed and the clear supernatant is used as such or in freeze-dried form for the determination of α-amylase. If desired, these crude extracts can also be subjected to further purification. Since for the use for α-amylase determination, separation of the two enzymes is unnecessary, further purification preferably takes place with the use of a test in which the total activity of both enzymes is determined after each purification step by adding thereto an appropriate buffer, as well as maltose, nicotinamide-adenine-dinucleotide phosphate (NADP) and G6PDH, and measuring the formation of reduced NADP (NADPH). The enzymes MP and β-PGM are thereby preferably activated by adding α-glucose-1,6-diphosphate and divalent manganese ions, for example in the form of manganese sulphate or another appropriate organic or inorganic manganese salt.

Therefore, the present invention is also concerned with the use of maltose phosphorylase and/or β-phosphoglucomutase, which have been obtained by the process according to the present invention, as a crude extract or in enriched form for the determination of α-amylase, optionally with the addition of α-glucose-1,6-diphosphate and/or divalent manganese ions.

The present invention enables the two mentioned enzymes to be obtained in a substantially simpler and cheaper manner and especially in a form in which they can be used directly, without previous separation, for the determination of α-amylase, the carrying out of such a determination thereby being substantially simplified.

The following Examples are given for the purpose of illustrating the present invention:

EXAMPLE 1

The micro-organisms mentioned in the following Table were cultured in a medium containing 1% maltose according to the procedure described by Kamogawa (Agr. Biol. Chem., 37, 2813/1973) and thereafter digested by high pressure dispersion. After centrifuging off insoluble material, the crude extract obtained was tested directly for its suitability for determining α-amylase according to the following reaction sequence:

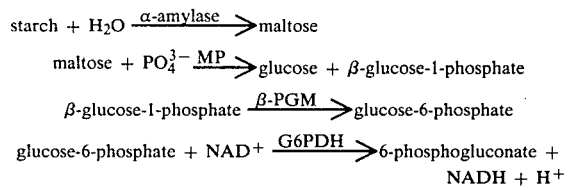

In order to ascertain the suitability of the crude extract, use was made of the following test batch:
3.4 ml. 0.1 M phosphate buffer+α-glucose-1,6,-diphosphate (c=0.05), pH 6.5
0.1 ml. MnSO₄, 1%
1.0 ml. 0.2 M maltose (Merck, for biochemical purposes)
0.5 ml. crude extract
Incubation: 1 hour at 37° C.
Stop: 1 ml. sample-3 minutes/100° C.; then centrifugation; 0.25 ml. supernatant employed in the following determination:
modified α-glucose-6-phosphate test:
2.54 ml. 0.3 M TRA buffer, pH 7.6
0.1 ml. 0.1 M MgCl₂
0.1 ml. NADP (c=10)
0.25 ml. supernatant
Start: 0.01 ml. G6PDH (c=1)
T=25°; measurement of $\Delta E_{366}$
The following Table shows the results obtained:

TABLE 1

| micro-organism used | | E (NADPH)[1] |
|---|---|---|
| Lactob. brevis | NCIB 8836 | 0.850 |
| Lactob. plantarum | DSM 20174 | 0.675 |
| Lactob. reuteri | DSM 20016 | 0.252 |
| Lactob. brevis | NCIB 8561 | 0.150 |
| Lactob. brevis | NCIB 8662 | 0.100 |
| Lactob. plantarum | DSM 43 | 0.090 |
| Streptococcus spec. | DSM 1118 | 0.115 |
| Streptococcus spec. | DSM 1119 | 0.125 |
| Streptococcus spec. | DSM 1120 | 0.210 |
| Streptococcus spec. | DSM 1121 | 0.110 |

[1] ΔE correlated directly with the MP/β-PGM activity

EXAMPLE 2

A reagent was used which had the following composition:

| | |
|---|---|
| phosphate buffer | 20 mM; pH 6.5 |
| NAD | 2 mM |
| maltotetraose | 10 mM |
| soluble starch | — |
| glucose-1,6-diphosphate | traces |
| crude extract from Lactob. plantarum DSM 20174 containing maltose phosphorylase and | 3 U/ml. |
| β-phosphoglucomutase | 1 U/ml. |
| G6PDH (Leuconostoc mesenteroides) dissolved in water | 9 U/ml. |

The solution obtained was incubated at 30° C. and mixed with the sample solution. After 5 minutes preincubation, the extinction difference was measured in a photometer at Hg 334 nm over 5 min. For 2.0 ml. reagent and 0.10 ml. sample, there applies the following formula for calculating the activity of the α-emylase in the sample:

$$U/l = \Delta E/min \times \frac{2.1 \times 1000}{6.18 \times 0.1 \times 2} = \Delta E/min. \times 1699$$

Using the above reagent for five different human sera, the following values were found:

TABLE 2

| serum | α-amylase | |
|---|---|---|
| 1 | 23.5 | U/l. |
| 2 | 88 | U/l. |
| 3 | 100 | U/l. |
| 4 | 120 | U/l. |
| 5 | 146 | U/l. |

It will be understood that the specification and examples are illustrative but not limitative of the present invention and that other embodiments within the spirit and scope of the invention will suggest themselves to those skilled in the art.

What is claimed is:

1. Process for obtaining an enzyme preparation comprising at least one member selected from the group consisting of maltose phosphorylase and β-phosphoglucomutase from micro-organisms, which process comprises extracting said enzyme preparation from a micro-organism selected from the group consisting of *Lactobacillus brevis* DSM 20054, NCIB 8836, 8561 and 8562, *Lactobacillus plantarum* DSM 20174 and 43, *Lactobacillus reuteri* DSM 20016, *Lactobacillus fermentum* DSM 20052, *Streptococcus spec.* DSM 1118, DSM 1119, DSM 1120 and DSM 1121.

2. Process as claimed in claim 1, wherein said enzyme is maltose phosphorylase.

3. Process as claimed in claim 1, wherein said enzyme is β-phosphoglucomutase.

4. Process for determining α-amylase which comprises contacting a sample suspected of containing α-amylase with starch and an enzyme preparation comprising maltose phosphorylase and β-phosphoglucomutase from a micro-organism selected from the group consisting of *Lactobacillus brevis* DSM 20054, NCIB 8836, 8561 and 8562, *Lactobacillus plantarum* DSM 20174 and 43, *Lactobacillus reuteri* DSM 20016, *Lactobacillus fermentum* DSM 20052, *Streptococcus spec.* DSM 1117, DSM 1119, DSM 1120 or DSM 1121,
splitting the maltose formed by means of said maltose phosphorylase, in the presence of phosphate, into glucose and β-glucose-1-phosphate,
converting the latter into α-glucose-6-phosphate by means of said β-phosphoglucomutase,
using said α-glucose-6-phosphate, in the presence of glucose-6-phosphodehydrogenase, to reduce nicotinamideadenine dinucleotide and determining the NADH formed as a measure of the initial α-amylase activity.

5. Process as claimed in claim 4, wherein the said enzyme is activated by adding α-glucose-1,6-diphosphate.

6. Process as claimed in claim 4, wherein the said enzyme is activated by adding divalent manganese ions.

7. Process as claimed in claim 4, wherein said enzyme comprises a crude extract from said micro-organisms.

8. Reagent composition for determining α-amylase which reagent composition comprises
an enzyme preparation comprising maltose phosphorylase and β-phosphoglucomutase from a micro-organism selected from the group consisting of *Lactobacillus brevis* DSM 20054, NCIB 8836, 8561 and 8562, *Lactobacillus plantarum* DSM 20174 and 43, *Lactobacillus reuteri* DSM 20016, *Lactobacillus fermentum* DSM 20052, *Streptococcus spec.* DSM 1118, DSM 1119, DSM 1120 and DSM 1121;
soluble starch;
phosphate buffer;
glucose-6-phosphatedehydrogenase; and
nicotinamide-adenine dinucleotide.

9. Reagent composition as claimed in claim 8, also comprising at least one of α-glucose-1,6-diphosphate and divalent manganese ions to activate said enzyme.

10. Reagent composition as claimed in claim 8, wherein said enzyme comprises a crude extract from said micro-organisms.

* * * * *